US010959601B2

(12) United States Patent
Watanabe

(10) Patent No.: US 10,959,601 B2
(45) Date of Patent: Mar. 30, 2021

(54) ENDOSCOPE SYSTEM

(71) Applicant: OLYMPUS CORPORATION, Hachioji (JP)

(72) Inventor: Nobuyuki Watanabe, Kanagawa (JP)

(73) Assignee: OLYMPUS CORPORATION, Tokyo (JP)

( * ) Notice: Subject to any disclaimer, the term of this patent is extended or adjusted under 35 U.S.C. 154(b) by 509 days.

(21) Appl. No.: 15/838,730

(22) Filed: Dec. 12, 2017

(65) Prior Publication Data

US 2018/0110401 A1 Apr. 26, 2018

Related U.S. Application Data

(63) Continuation of application No. PCT/JP2015/069333, filed on Jul. 3, 2015.

(51) Int. Cl.
*A61B 1/00* (2006.01)
*A61B 5/06* (2006.01)
(Continued)

(52) U.S. Cl.
CPC ...... *A61B 1/00009* (2013.01); *A61B 1/00006* (2013.01); *A61B 1/0051* (2013.01);
(Continued)

(58) Field of Classification Search
None
See application file for complete search history.

(56) References Cited

U.S. PATENT DOCUMENTS

2007/0276184 A1* 11/2007 Okawa ............... A61B 1/04
  600/117
2008/0029688 A1* 2/2008 Yagi ............... H04N 5/343
  250/208.1
(Continued)

FOREIGN PATENT DOCUMENTS

EP  2 425 760 A1  3/2012
EP  2 497 406 A1  9/2012
(Continued)

OTHER PUBLICATIONS

International Search Report dated Aug. 18, 2015, issued in counterpart International Application No. PCT/JP2015/069333, w/English translation (4 pages).
(Continued)

*Primary Examiner* — Timothy J Neal
(74) *Attorney, Agent, or Firm* — Westerman, Hattori, Daniels & Adrian, LLP

(57) ABSTRACT

For the purpose of improving the manipulability at the time of insertion and improving the ease of observation at the time of removal, according to the movement direction of an insertion portion with respect to a body cavity and a movement mode thereof, an endoscope system includes: an endoscope that is provided with an insertion portion that is inserted into a body cavity and an image acquisition part that acquires, at the distal end of the insertion portion, an image of the inside of the body cavity; an insertion/removal detector that detects a relative movement direction of the insertion portion with respect to the body cavity; an image generator that generates image information suitable for a movement mode of the insertion portion based on the relative movement direction detected by the insertion/removal detector; and an image display part that displays the image information generated by the image generator.

5 Claims, 13 Drawing Sheets

(51) Int. Cl.
*G02B 23/24* (2006.01)
*G01S 17/88* (2006.01)
*A61B 1/005* (2006.01)
*A61B 1/06* (2006.01)
*G01S 17/36* (2006.01)
*G01S 17/48* (2006.01)
*G02B 23/26* (2006.01)

(52) U.S. Cl.
CPC ........ *A61B 1/00096* (2013.01); *A61B 1/0661* (2013.01); *A61B 5/061* (2013.01); *G01S 17/88* (2013.01); *G02B 23/2476* (2013.01); *A61B 1/00165* (2013.01); *G01S 17/36* (2013.01); *G01S 17/48* (2013.01); *G02B 23/26* (2013.01)

(56) References Cited

U.S. PATENT DOCUMENTS

| | | | | |
|---|---|---|---|---|
| 2008/0188716 | A1* | 8/2008 | Heckele | A61B 1/04 600/166 |
| 2011/0230712 | A1* | 9/2011 | Matsuura | A61B 1/00078 600/106 |
| 2011/0273549 | A1 | 11/2011 | Kase et al. | |
| 2011/0275889 | A1 | 11/2011 | Kase et al. | |
| 2013/0222563 | A1 | 8/2013 | Kitano | |
| 2015/0363942 | A1 | 12/2015 | Mitsui | |

FOREIGN PATENT DOCUMENTS

| | | |
|---|---|---|
| EP | 2630907 A1 | 8/2013 |
| EP | 2962621 A1 | 1/2016 |
| JP | 2003-199707 A | 7/2003 |
| JP | 2009-136353 A | 6/2009 |
| JP | 4856286 B2 | 1/2012 |
| JP | 4884567 B2 | 2/2012 |
| JP | 4979271 B2 | 7/2012 |
| JP | 2013-172908 A | 9/2013 |
| JP | 2014-113416 A | 6/2014 |
| JP | 2014-161537 A | 9/2014 |
| JP | 2015-91467 A | 5/2015 |

OTHER PUBLICATIONS

Office Action dated Jul. 9, 2019, issued in counterpart JP application No. 2017-526809, with English translation (9 pages).

* cited by examiner

ENDOSCOPE SYSTEM

CROSS-REFERENCE TO RELATED APPLICATIONS

This is a continuation of International Application PCT/JP2015/069333, with an international filing date of Jul. 3, 2015, which is hereby incorporated by reference herein in its entirety.

TECHNICAL FIELD

The present invention relates to an endoscope system.

BACKGROUND ART

In colonoscopy, an insertion portion of an endoscope is inserted into a body cavity, and, while the insertion portion is being removed therefrom, images of an inner wall of the body cavity, that are acquired by an image acquisition part disposed on a distal end of the insertion portion, are observed. The presence or absence of a lesion or the state thereof is diagnosed from information of the shape and/or the color of the inner wall of the body cavity in the images. Thus, there are known endoscope systems in which the illumination method and image-acquisition angle of view are switched between when the insertion portion is inserted into and, removed from the body cavity (for example, see PTL 1 and PTL 2).

CITATION LIST

Patent Literature

{PTL 1} Publication of Japanese Patent Kb. 4856286
{PTL 2} Publication of Japanese Patent No. 4884567
{PTL 3} Publication of Japanese Patent No. 4979271

SUMMARY OF INVENTION

Technical Problem

In the endoscope systems of PTLs 1 and 2, at the time of insertion and removal of the insertion portion, a portion being gazed by an operator is displayed in an enlarged manner, or the luminance at the portion being gazed by the operator is relatively increased, thereby making it possible to improve the manipulability at the time of insertion and to improve the ease of observation at the time of removal.

Although PTL 3 discloses a technique for making the frame variable according to the speed of insertion, in particular, when operating a colonoscopy objects to be focused on differ between the time of insertion and the time of observation during removal. At the time of insertion, irrespective of the speed of insertion, global information, such as the shapes of folds, is always taken into account to predict the next tasks, such as advancing or retracting, turns, angles, etc.

The present invention provides an endoscope system capable of improving the manipulability at the time of insertion and improving the ease of observation at the time of removal according to the movement direction of the insertion portion with respect to the body cavity and the movement mode thereof.

Solution to Problem

According to one aspect, the present invention provides an endoscope system including: an endoscope that is provided with an insertion portion that is configured to be inserted into a body cavity and an image acquisition part that is configured to acquire, at a distal end of the insertion portion, an image of the inside of the body cavity; an insertion/removal detector that is configured to detect a relative movement direction of the insertion portion with respect to the body cavity; an image generating part that is configured to generate image information suitable for a movement mode of the insertion portion based on the relative movement direction detected by the insertion/removal detector; and an image display part that is configured to display the image information generated by the image generator.

In the above-described aspect may further include an image-acquisition controller that is configured to control the image-acquisition part, wherein, based on the relative movement direction, the image-acquisition controller may control a frame rate of the image acquisition part or the image generator may process a tone of the image acquired by the image acquisition part.

In the above-described aspect may further include an image-acquisition controller that is configured to control the image-acquisition part, wherein based on the relative movement direction, the image-acquisition controller may control a frame rate of the image acquisition part.

In the above-described aspect, based on the relative movement direction, the image generator may process a tone of the image acquired by the image acquisition part.

In the above-described aspect, the image-acquisition controller may control the image acquisition part such that the frame rate is increased, when the relative movement direction detected by the insertion/removal detector is a direction of the insertion portion being inserted into the body cavity, compared with when the relative movement direction detected by the insertion/removal detector is a direction ox the insertion portion being removed from the body cavity.

In the above-described aspect, the image-acquisition controller may control the image acquisition part such that signals of a plurality of pixels are added and then output when the relative movement direction detected by the insertion/removal detector is the direction of the insertion portion being inserted into the body cavity.

In the above-described aspect, the image generator may process an image acquired by the image acquisition part such that the image has a low-brightness-visibility emphasizing tone when the relative movement direction detected by the insertion/removal detector is the direction of the insertion portion being inserted into the body cavity, compared with when the relative movement direction is the direction of the insertion portion being removed from the body cavity.

In the above-described aspect, the image generator may process an image acquired by the image acquisition part such that the image has a medium-brightness-visibility emphasizing tone when the relative movement direction detected by the insertion/removal detector is the direction of the insertion portion being removed from the body cavity, compared with when the relative movement direction is the direction, of the insertion portion, being inserted into the body cavity.

The above-described aspect may further include a range sensor that is configured to obtain distance information from the distal end of the insertion portion to the body cavity, wherein, only when the relative movement direction detected by the insertion/removal detector is the direction of the insertion portion being inserted into the body cavity, the image generator may generate image information that includes the distance information obtained by the range sensor.

DESCRIPTION OF EMBODIMENT

An endoscope system 1 according to one embodiment of the present invention will be described below with reference to the drawings.

Figure 1:
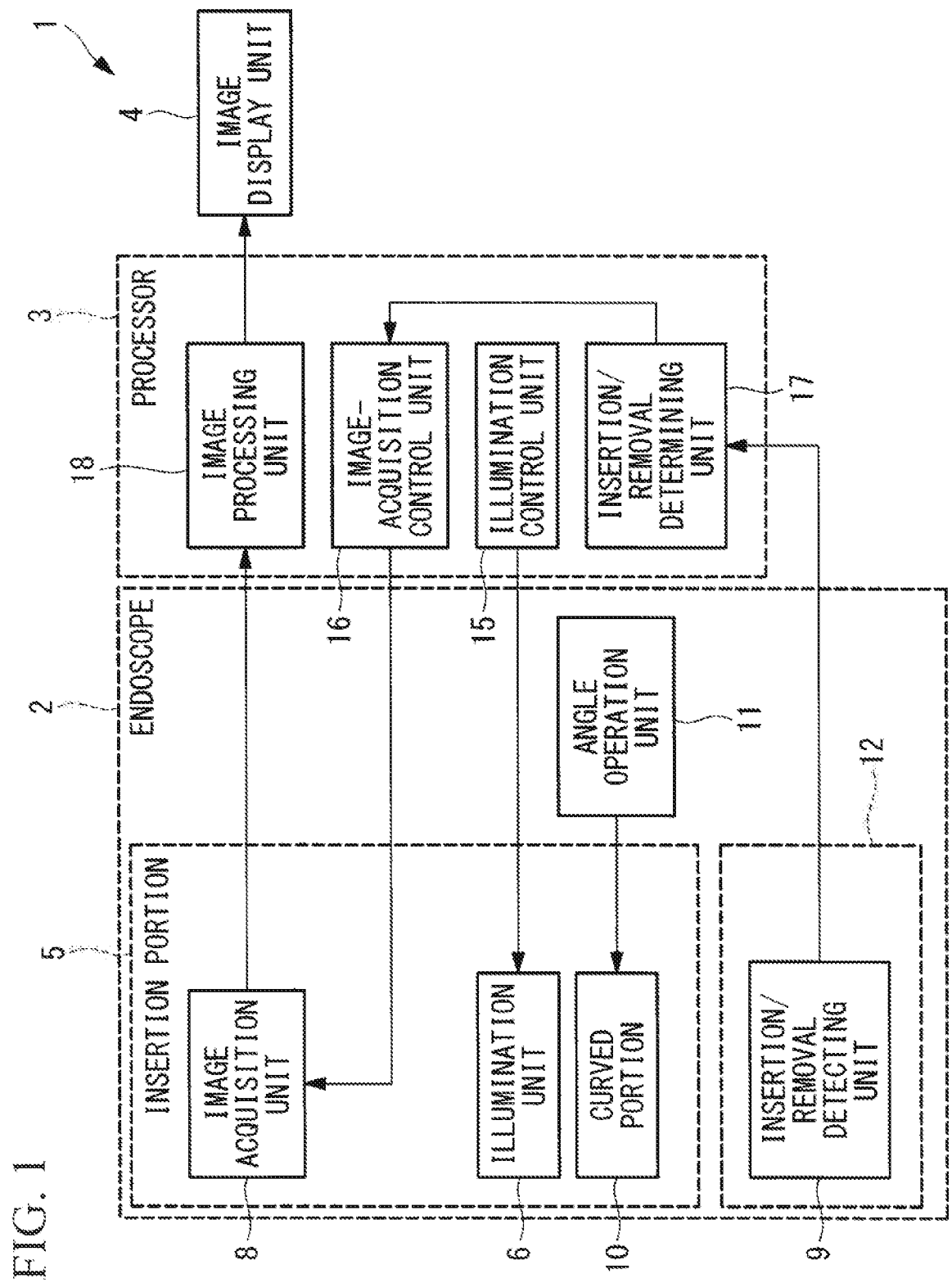
FIG. 1 is a view showing the overall configuration of an endoscope system according to one embodiment of the present invention.

As shown in FIG. 1, the endoscope, system 1 of this embodiment is provided with an endoscope 2, a processor 3 that is configured to control the endoscope 2 and that processes information obtained by the endoscope 2, and an image display part 4 that is configured to display a processing result obtained by the processor 3. The image display part 4 may include at least one of a monitor, a display screen and a display.

As shown in FIG. 1, the endoscope 2 is provided with: an insertion portion 5 that is configured to foe inserted into a body cavity of a patient; an illumination part 6 that Is configured to radiate, from a distal end of the insertion portion 5, illumination light onto the inside of the body cavity; an image acquisition part 3 that is configured to acquire an image of the inside of the body cavity via an image-acquisition optical system (not shown) disposed at the distal end of the insertion portion 5; and an insertion/removal detector 9 that is configured to detect whether the insertion portion 5 is being inserted or is being removed. In the figure, reference sign 11 denotes an angle operator that is configured to move a curved portion 10 provided at the distal end of the insertion portion 5.

The image acquisition part 8 is provided with an image acquisition element 7, such as a CCD, that can change the frame rate. In this embodiment, the frame rate can be switched between two states, i.e., 120/second and 60/second.

The image acquisition part 8 can switch pixel addition ON and OFF. Specifically, when pixel addition is in the OFF state, the image acquisition part 8 outputs image signals from all pixels as individual image signals. When pixel addition is switched to the ON state, the image acquisition part 8 adds signals of a plurality of adjacent pixels, for example, 2×2=4 pixels, and outputs the sum as an image signal of one pixel.

Figure 2:
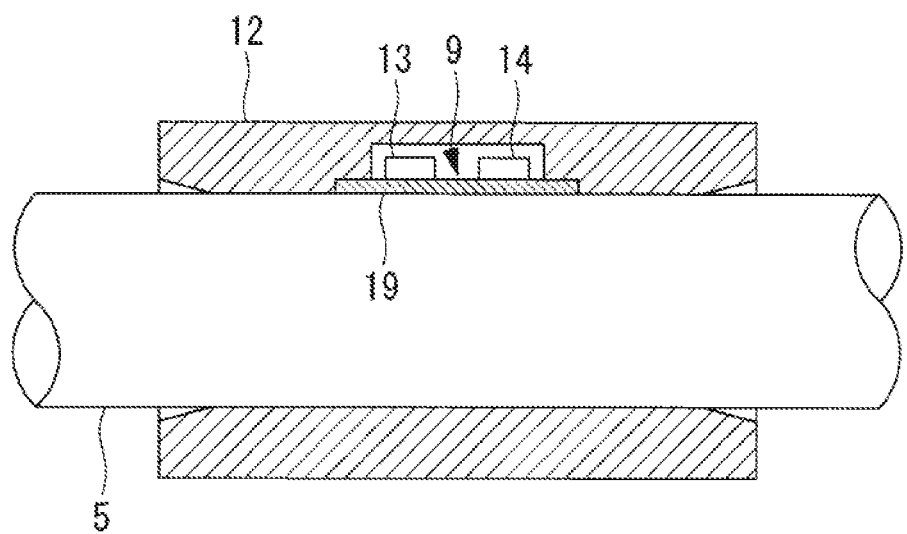
FIG. 2 is a view showing an example insertion/removal detector provided in the endoscope system shown in FIG. 1.

As shown in FIG. 2, it is possible to adopt, as the insertion/removal detector 9, for example, a unit in which a light-emitting part 13 that emits light to an outer surface of the insertion portion 5 and a light-receiving part 14 that receives reflected light, of the light emitted from the light-emitting part 13, reflected at the outer surface of the insertion portion 5 are provided on an overtube 12 that is fixed with respect to the body cavity at an entrance or the like of the body cavity, and through which the insertion portion 5 passes. According to the insertion/removal detector 9, by using the fact that a shift between the timing of light emission from the light-emitting part 13 and the timing of light reception at the light-receiving part 14 changes according to the movement direction and the movement speed of the insertion portion 5, it is possible to detect a relative movement direction indicating that the insertion portion 5 is being inserted into the body cavity or is being removed therefrom. Reference sign 19 denotes a window member made of an optically transparent material.

The processor 3 is provided with an illumination control unit 15 that controls the illumination part 6 of the endoscope 2; an image-acquisition controller 16 that controls the image acquisition part 8; an insertion/removal determining part 17 that determines the relative movement direction of the insertion portion 5 with respect to the body cavity on the basis of an output from the insertion/removal detector 9; and an image processor (image generator) 18 that processes image signals acquired by the image acquisition part 8 to generate an image. The image generated by the image processor 18 is sent to the image display part 4 and is displayed thereon.

As a result of the determination performed by the insertion/removal determining part 17, if it is determined that the insertion portion 5 is in a state being inserted into the body cavity, the image-acquisition controller 16 instructs the image acquisition part 8 to switch the frame rate to 120/second and to switch pixel addition to the ON state.

On the other hand, as a result of the determination performed by the insertion/removal determining part 17, if it is determined that the insertion portion 5 is in a state in which it is being removed from the body cavity, the image-acquisition controller 16 instructs the image acquisition part 8 to switch the frame rate to 60/second and to switch pixel addition to the OFF state.

When the insertion/removal detector 9 detects the same state for a predetermined period of time, the insertion/removal determining part 17 determines whether the insertion portion 5 is an inserting state or a removing state. The amount of insertion of the insertion portion 5 into the body cavity is accumulated on the basis of a detection signal obtained by the insertion/removal detector 9, and, after the amount of insertion exceeds a predetermined insertion amount, when the removing state lasts for the predetermined period of time, it may be determined that the state is switched to the removing state.

The operation of the thus-configured endoscope system 1 of this embodiment will be described below.

In order to observe the inside of the body cavity by using the endoscope system 1 of this embodiment, the overtube 12 is fixed in the vicinity of the entrance of the body cavity, the insertion portion 5 is made to pass through the overtube 12 and is inserted into the body cavity starting from the distal end thereof.

Figure 3:
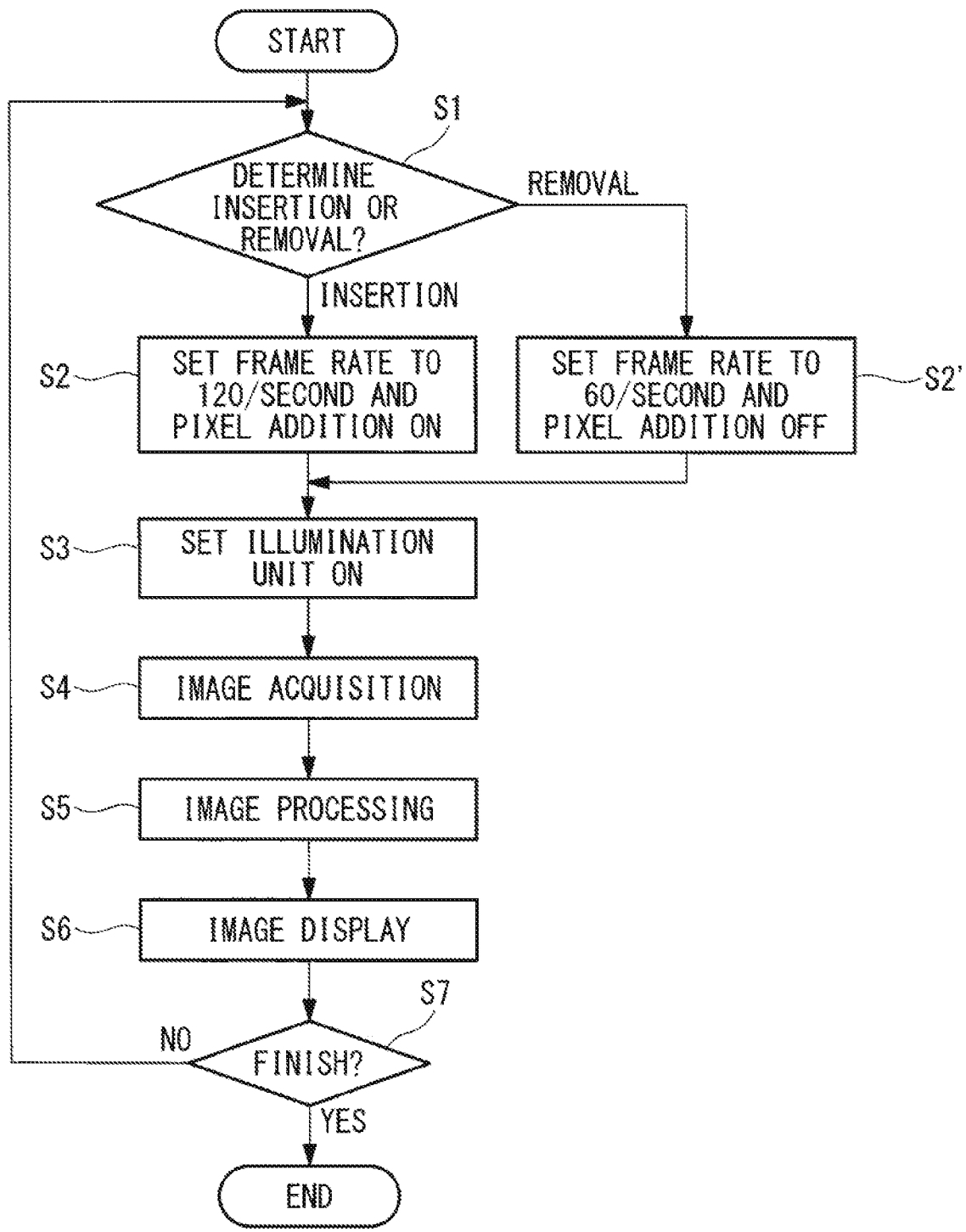
FIG. 3 is a flowchart for explaining the operation of the endoscope system shown in FIG. 1.

As shown in FIG. 3, first, it is determined whether the insertion portion 5 is being inserted into the body cavity or is being removed therefrom (Step S1). At the start of insertion of the insertion portion 5 into the body cavity, because the relative movement direction of the insertion portion 5 with respect to the body cavity is the direction of insertion, the image-acquisition controller 16 of the processor 3 outputs, to the image acquisition part 8, an instruction signal for setting the frame rate to 120/second and for setting pixel addition to the ON state (Step S2). Then, through activation of the illumination controller 15 of the processor 3, the illumination part 6 is activated to radiate illumination light from the distal end of the insertion portion 5 toward the inside of the body cavity located in front thereof (Step S3).

Accordingly, reflected light of the illumination light reflected at the inner surface of the body cavity is captured by the image acquisition part 8 via the image-acquisition optical system (Step S4), and an acquired image is processed by the image processor 18 of the processor 3 (Step S5) and is then displayed on the image display part 4 (Step S6).

In this case, for example, in the case of colonoscopy, at the time of insertion of the insertion portion 5 into the body cavity, since the prime concern of an operator is to cause the insertion portion 5 to rapidly reach the end of the body cavity, for example, the position of the cecum, the operator adopts a movement mode in which the angle operation part 11 is frequently operated to frequently curve the curved portion 10 and, push and pull the insertion, portion 5, thus inserting the insertion portion 5 while searching for an insertion, direction. Therefore, the operator does not observe the state of the inner wall of the body cavity during the inserting state, and thus, images of the inner wall of the body cavity need not be finely acquired.

According to the endoscope system 1 of this embodiment, at the time of insertion of the insertion portion 5 into the body cavity, the frame rate is set at a high value; thus, there is an advantage in that, even if frequent changes of images are caused due to swinging or movement of the distal end of the insertion portion 5 through the frequent operations of the angle operation part 11, it is possible to display a smooth moving image on the image display part 4 and to assist a smooth insertion work to the operator.

In particular, at the same time as the higher frame rate is set, the number of image signals is reduced through pixel addition; thus, it is possible to rapidly perform processing and to prevent delay of displayed images, thus making it possible to display a smoother moving image. Since the sensitivity is improved through pixel addition, there is an advantage in that a reduction in exposure time due to the higher frame rate is compensated for, thus making it possible to acquire a bright image. Because a far-side area in the body cavity that is gazed by the operator, in the image, is far from the distal end of the insertion portion 5 and is thus dark, the entire image is made bright, thereby improving the manipulability, which is advantageous.

In this embodiment, as long as the inserting state of the insertion portion 5 is detected by the insertion/removal detector 9, which is provided on the overtube 12, high-frame-rate image capturing and pixel addition are performed, thus making it possible to continuously obtain the above-described effects.

Then, it is determined whether observation is finished (Step S7). If observation is not finished, the process from Step S1 is repeated.

On the other hand, after the insertion portion 5 reaches the end of the body cavity, the operator performs the action of removing the insertion portion 5 from the body cavity. Accordingly, if the insertion/removal detector 9, which is provided on the overtube 12, detects that the insertion portion 5 is moving in the direction in which it is in removing from the body cavity (Step S1), the image-acquisition controller 16 causes the image acquisition part 8 to switch the frame rate to 60/second and to switch pixel addition to the OFF state (Step S2').

In the case of colonoscopy, the operator adopts a movement mode of the endoscope 2 in which the presence or absence of a lesion or the state of the lesion on the inner wall of the body cavity is observed in detail while removing the endoscope 2.

Therefore, the movement, of the insertion portion 5 is slower than that during insertion thereof into the body cavity, and, even if the frame rate is reduced, the smoothness of a moving image is not lost.

Furthermore, by switching pixel addition to the OFF state, there is an advantage in that it is possible to acquire a high-resolution image using image signals from all pixels and to perform, in detail on the image displayed on the image display part 4, confirmation of the presence or absence of a lesion and observation of the state thereof.

In this case, the number of images acquired per unit, time is reduced by reducing the frame rate, thus making it possible to prevent delay of processing even if each image is made to have a high resolution.

Note that, in this embodiment, although 60/second and 120/second are adopted as frame rates, it is needless to say that the frame rates are not limited thereto.

In this embodiment, although the insertion/removal detector 9, which is provided on the overtube 12, detects the direct ion of movement of the insertion portion 5 with respect to the body cavity, the present invention is not limited thereto.

Figure 4:
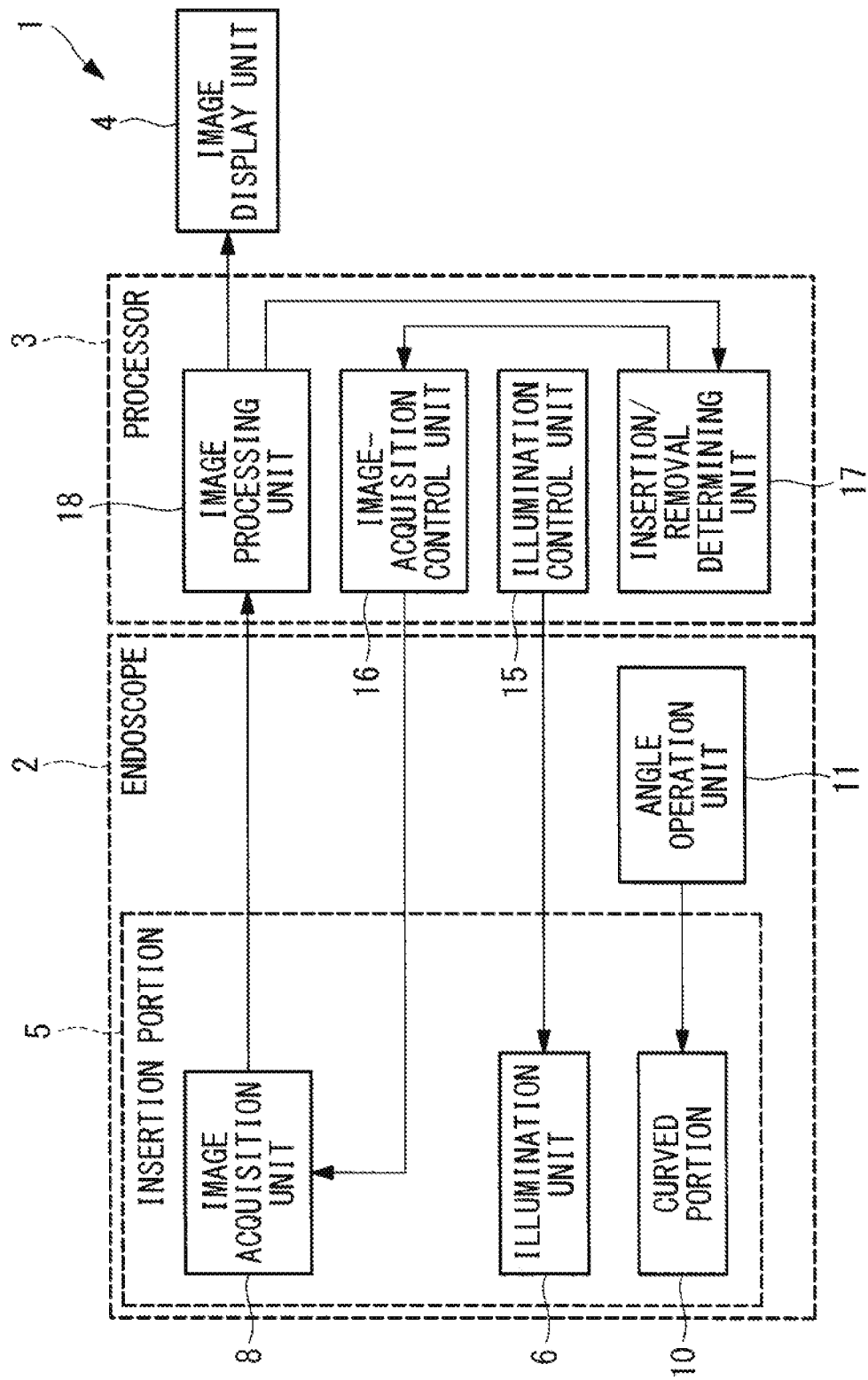
FIG. 4 is a view showing the overall configuration of a first modification of the endoscope system shown in FIG. 1.

For example, as shown in FIG. 4, the image acquisition part 8 may also serve as the insertion/removal detector 9, and the insertion/removal determining part 17 may determine arrival at the end of the body cavity according to the pattern of an image (or the pattern of continuous images) acquired by the image acquisition part 8 and generated by the image processor 18. For example, when arrival at the cecum is detected according to the pattern of an image, the state before arrival at the cecum is determined as the inserting state, and the state after arrival at the cecum is determined as the removing state.

Figure 5:
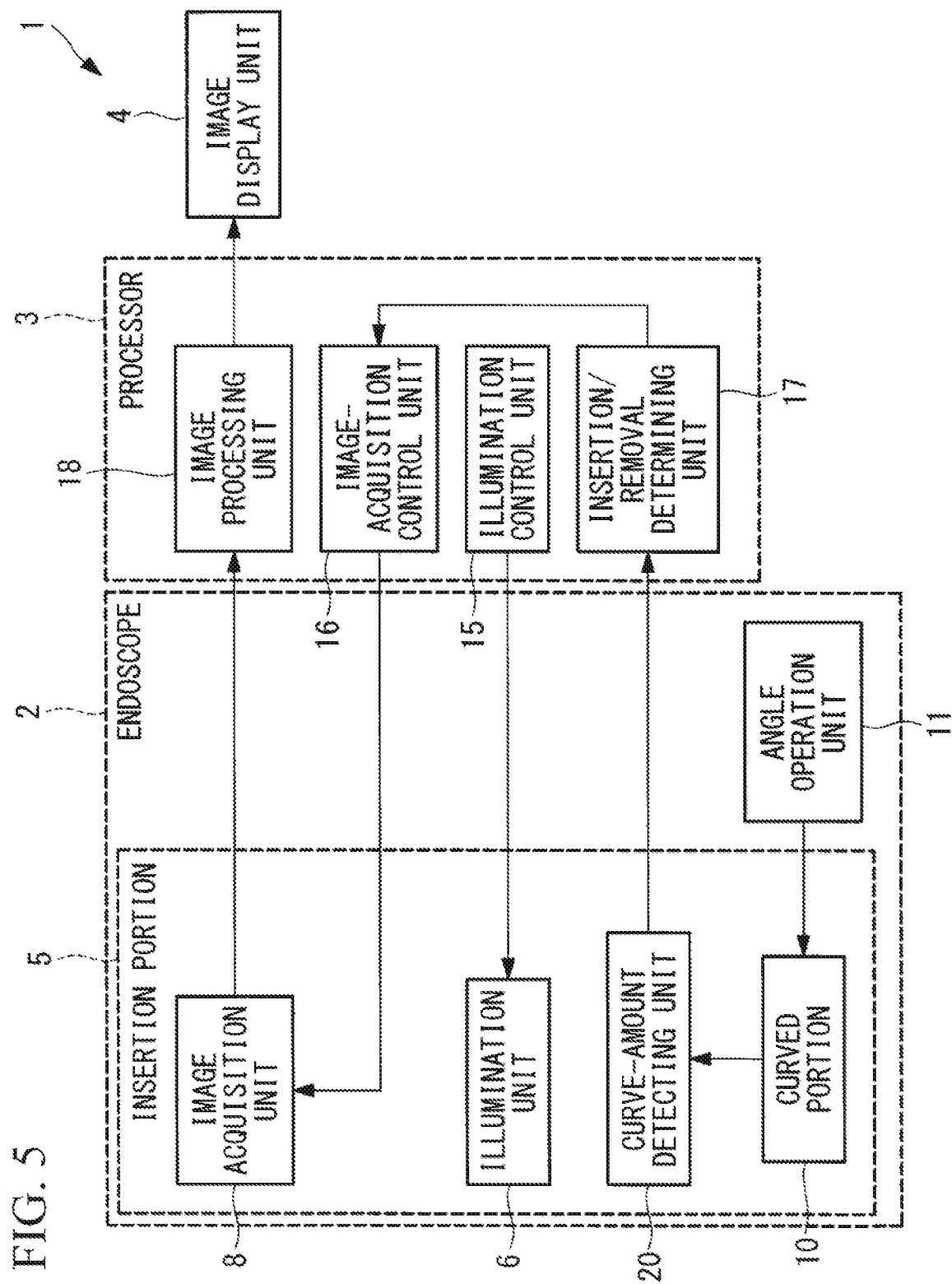
FIG. 5 is a view showing the overall configuration of a second modification of the endoscope system shown in FIG. 1.
Figure 6:
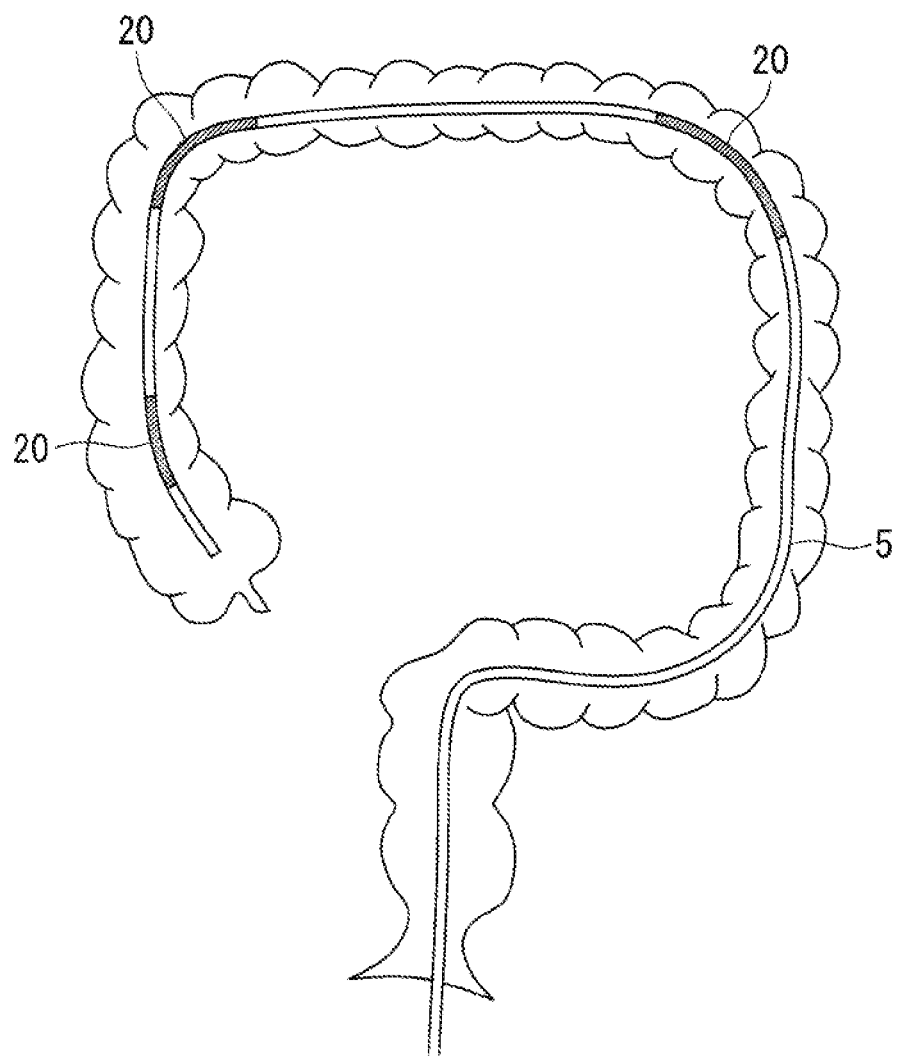
FIG. 6 is a view, showing an example insertion/removal detector provided in an endoscope system shown in FIG. 5.

As shown in FIGS. 5 and 6, as the insertion/removal detector 9, sensors (curve-amount detector) 20 that detect curve amounts of the insertion portion 5 may be provided at respective positions of the insertion portion 5, and the insertion/removal determining part 17 may estimate the shape of the insertion portion 5 on the basis of the outputs from the sensors 20, thereby determining arrival at the end of the body cavity.

Figure 7:
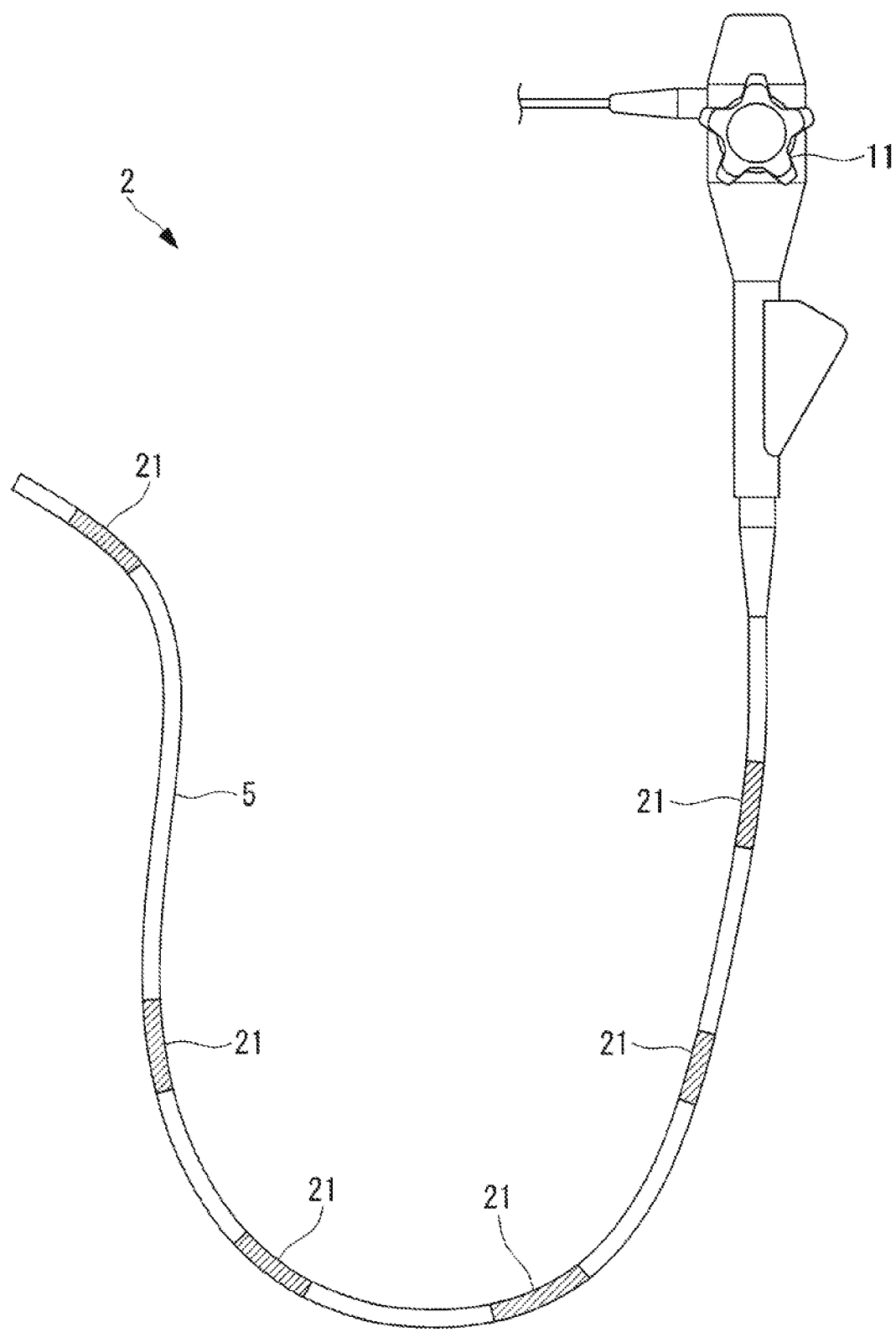
FIG. 7 is a view for explaining an insertion/removal detector according to a third modification of the endoscope system shown in FIG. 1.

As shown in FIG. 7, it is also possible to dispose pressure sensors 21 that individually detect that they are being grasped by the operator, at intervals in the longitudinal direction of the insertion portion 5, and to determine that the insertion portion 5 has arrived at the end of the body cavity according to the detection order and the detected positions detected by the pressure sensors 21. Specifically, at the time of insertion of the insertion portion 5, detections by the pressure sensors 21 are sequentially performed starting from the pressure sensor 21 disposed at the distal end of the insertion portion 5, and, after detection by the pressure sensor 21 disposed at a predetermined position is performed, when the detection order reverses toward the distal end, it is possible to determine that the insertion portion 5 has been switched to the removing state.

Whether the insertion portion 5 has been switched to the removing state can be determined on the basis of a detection result that is obtained by the pressure sensors 21 on the insertion portion 5 and that indicates whether the force is applied in the insertion direction or in the removal direction.

Figure 8A:
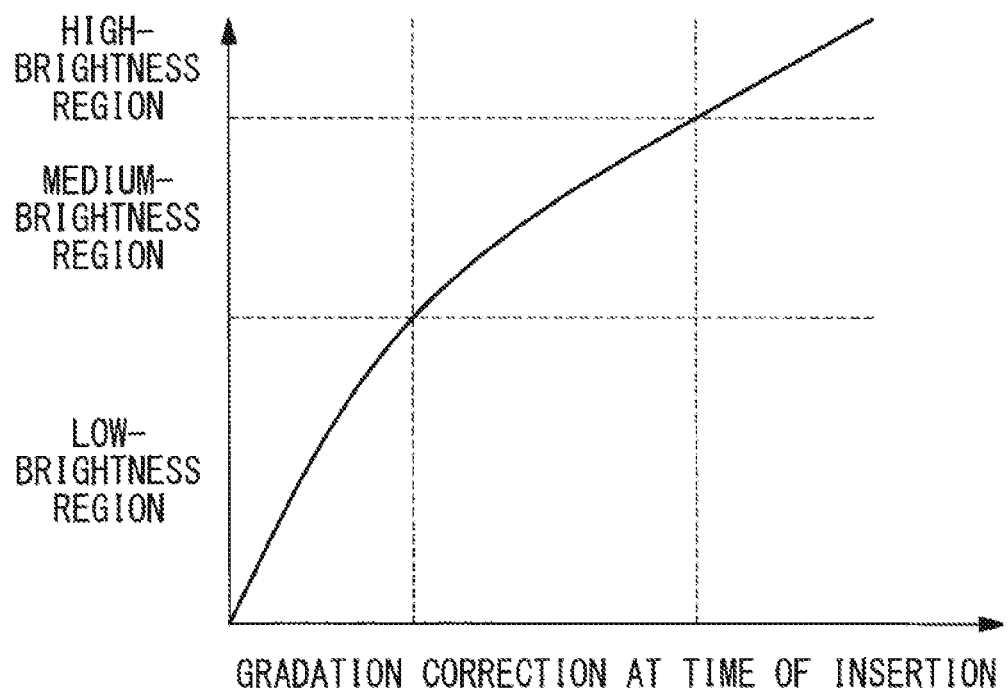
FIG. 8A is a view showing an example tone used by the endoscope system shown in FIG. 1 when the insertion portion is inserted.
Figure 8B:
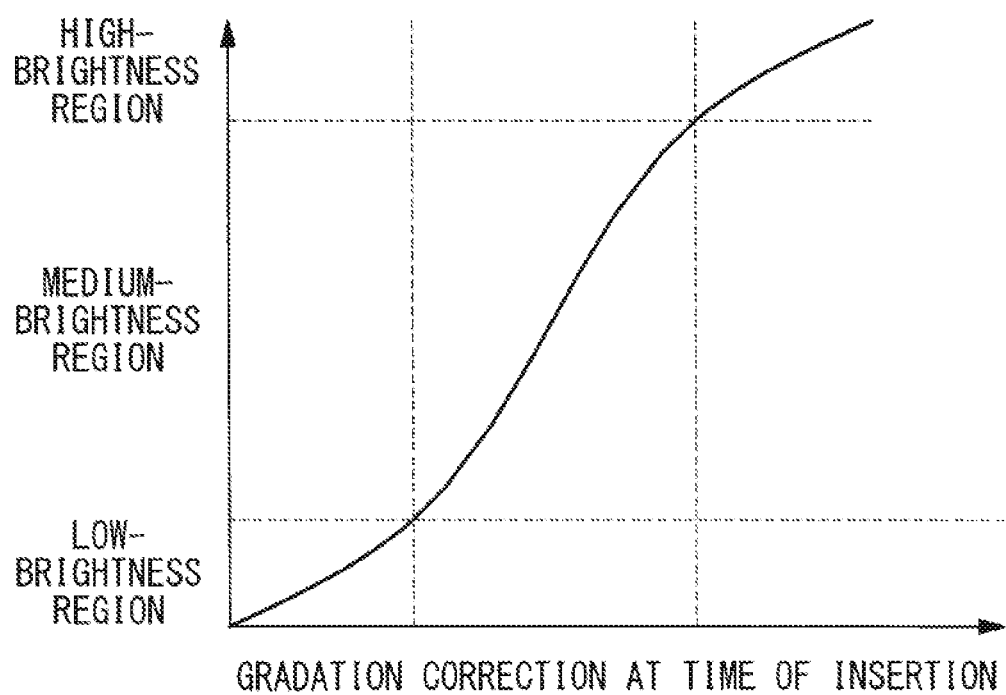
FIG. 8B is a view showing: an example tone used by the endoscope system shown in FIG. 1 when the insertion portion is in removing.

In this embodiment, the frame rate is switched depending on whether or not the insertion, portion 5 is in the inserting state, in addition to the embodiment, it is also possible to perform gradation correction in the image processor 18, as shown in FIGS. 8A and 8B.

Specifically, it is preferable to adopt a tone that, increases the number of low-brightness gradation values, as shown in FIG. 8A, when the insertion portion 5 is in the inserting state and to adopt, a tone that increases the number of medium-brightness gradation values, as shown in FIG. 8B, when the insertion portion 5 is in the removing state.

By doing so, when the insertion portion 5 is in the inserting state, the low-brightness-visibility emphasizing tone is used, thus increasing the number of the gradation values in a low-brightness region and making it possible to accurately determine the traveling direction of the insertion portion 5 on the basis of a high-definition image in which the contrast is increased by assigning many gradation values to the low-brightness region. In particular, in conjunction with pixel addition, the noise at low intensities is reduced even when the number of the gradation values from the low brightness to the medium brightness is increased, as shown in FIG. 8A; thus, it is possible to obtain the effect of improving the robustness (of making noise less noticeable) with, respect to the gradation correction.

When the insertion portion 5 is in the removing state, image processing is performed so as to produce a medium-brightness-visibility emphasizing tone; thus, there is an advantage in that high-definition observation of a lesion portion can be performed by assigning many gradation values to a medium-brightness region.

In this embodiment, although the frame rate is switched depending on whether the insertion portion 5 is in the inserting state or in the removing state with respect to the body cavity, instead of this or in addition thereto, it is also possible to detect, in the inserting state, the distances from the image acquisition part 8, which is disposed at the distal end of the insertion portion 5, to respective sections in the body cavity and to display the distance information on the image display part 4.

The distances can be detected by using the following methods.

Figure 9:
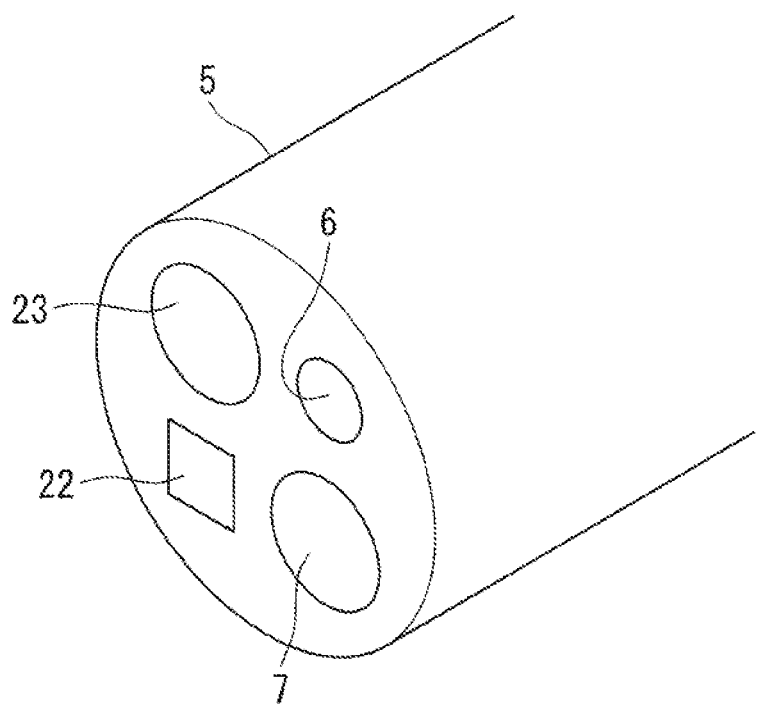
FIG. 9 is a perspective view showing a distal end of an insertion portion according to a fourth modification of the endoscope system shown in FIG. 1.

For example, as shown in FIG. 9, a distance-detection light source 22 that is formed of a near-infrared or infrared LED and a distance-detection image acquisition element (range sensor) 23, such as a CMOS image sensor, that captures light reflected at the inner surface of the body cavity and returning are provided at the distal end of the insertion portion 5.

Figure 10:
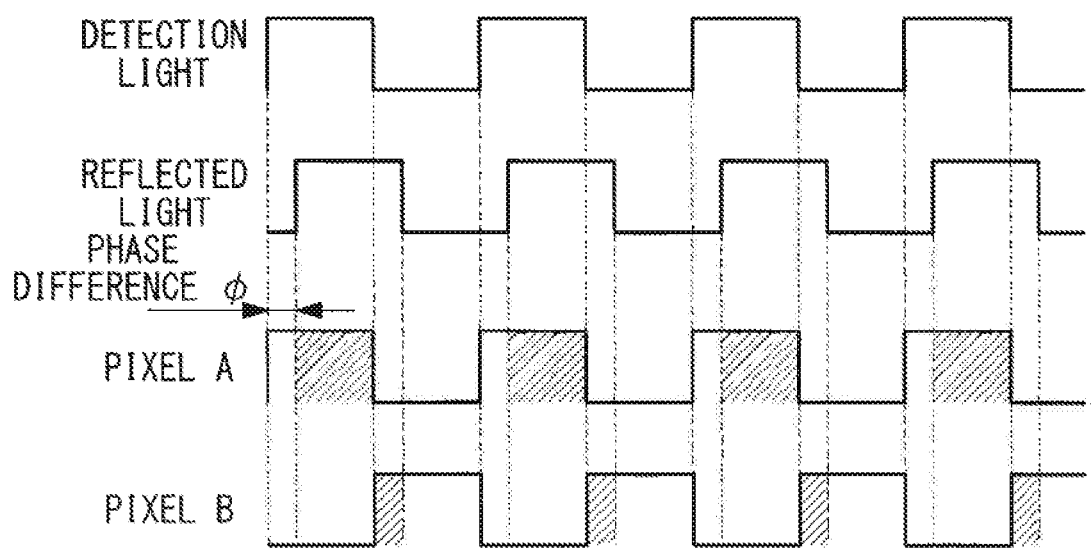
FIG. 10 is a view showing examples of illumination light, detection light, reflected light, and detection signals at respective pixels, the detection light being emitted for distance measurement in an endoscope system shown in FIG. 9.

As shown in FIG. 10, it is possible to use a time-of-flight (TOF) method in which pulsed detection light that is driven at a predetermined period is emitted, from the distance-detection light source 22, and the optical path lengths are estimated for pixels A and B on the distance-detection image acquisition element 23 on the basis of the phase difference φ between the detection light and reflected light reflected at the pixels A and B.

Figure 11:
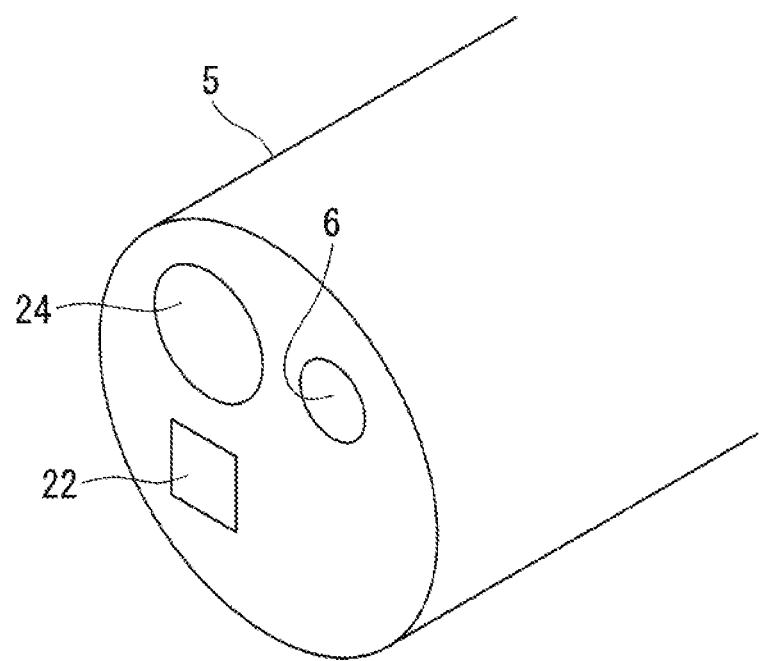
FIG. 11 is a perspective view showing another example of a distal end of an insertion portion in the endoscope system shown in FIG. 9.

The distance-detection image acquisition element 23 may be provided separately from the visible-light-observation image acquisition element 7, or, as shown in FIG. 11, a conation image acquisition element 24 may perform both visible-light observation and distance measurement.

When both visible-light observation and distance measurement are performed, pixels for visible-light observation and pixels for distance measurement may be arrayed at predetermined intervals on the same substrate.

Figure 12:
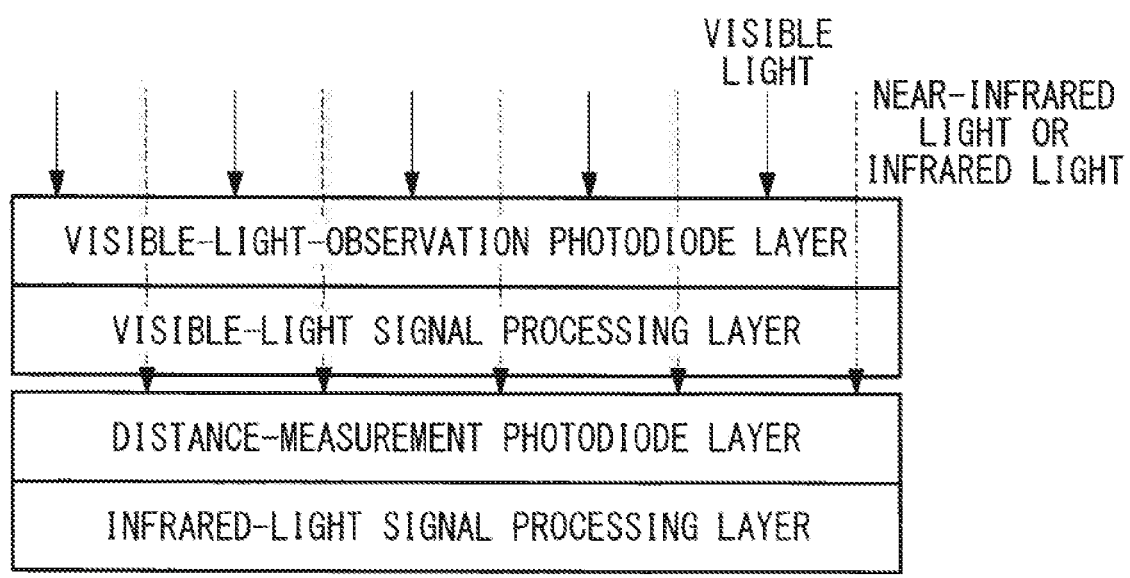
FIG. 12 is a view showing an example image acquisition, element used, in an endoscope system shown in FIG. 11.

Instead of this, by using the fact that near-infrared light or infrared light is transmitted through a thinned, silicon substrate, as shown in FIG. 12, distance-measurement photodiodes are arrayed on the layer under visible-light-observation photodiodes, thus making it possible to achieve a reduction in the diameter of the insertion portion 5 by reducing the area of a place where the image acquisition element is installed, which is advantageous.

Figure 13:
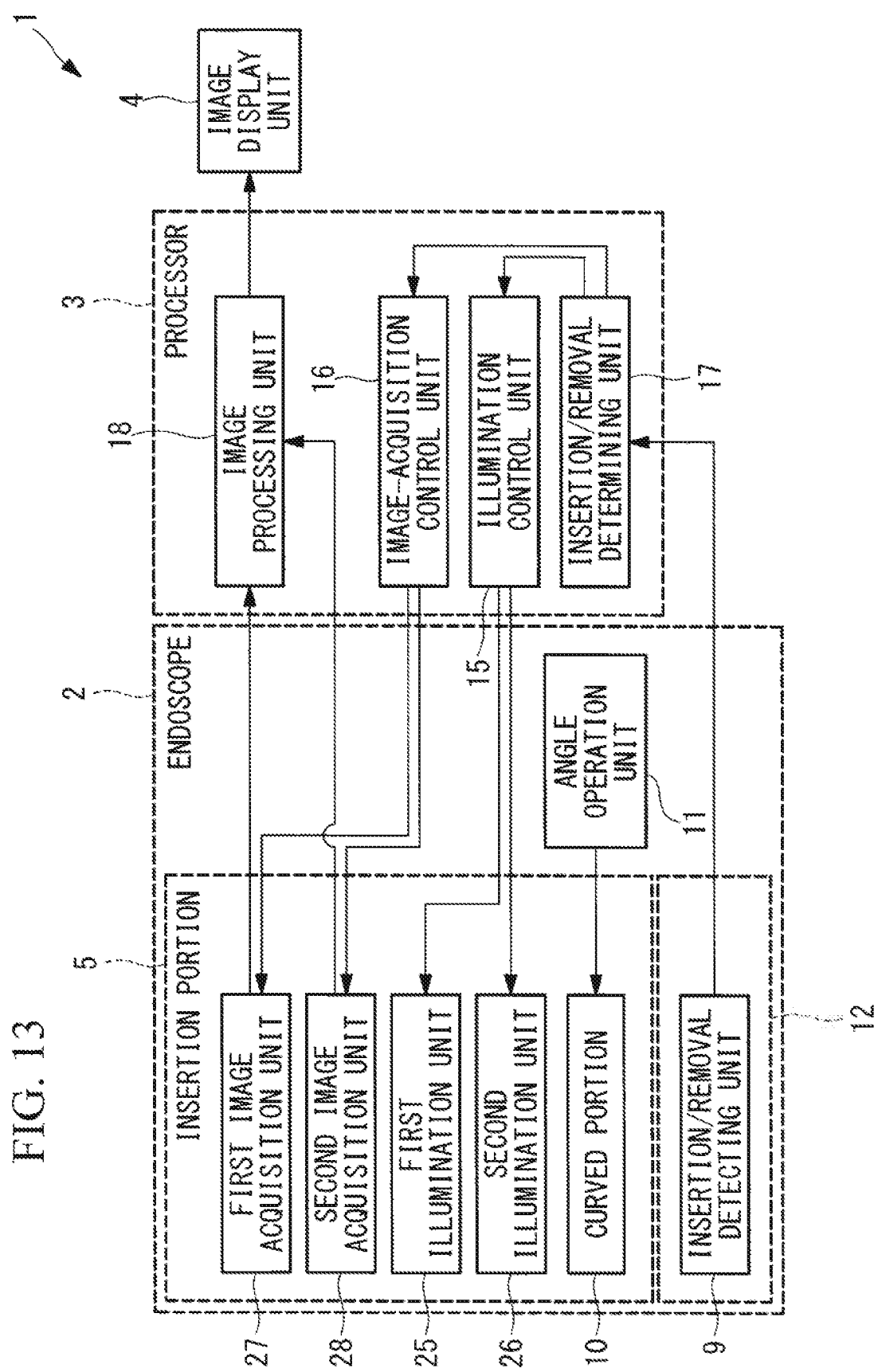
FIG. 13 is a view showing the overall configuration of the endoscope system, shown in FIG. 9.
Figure 14:
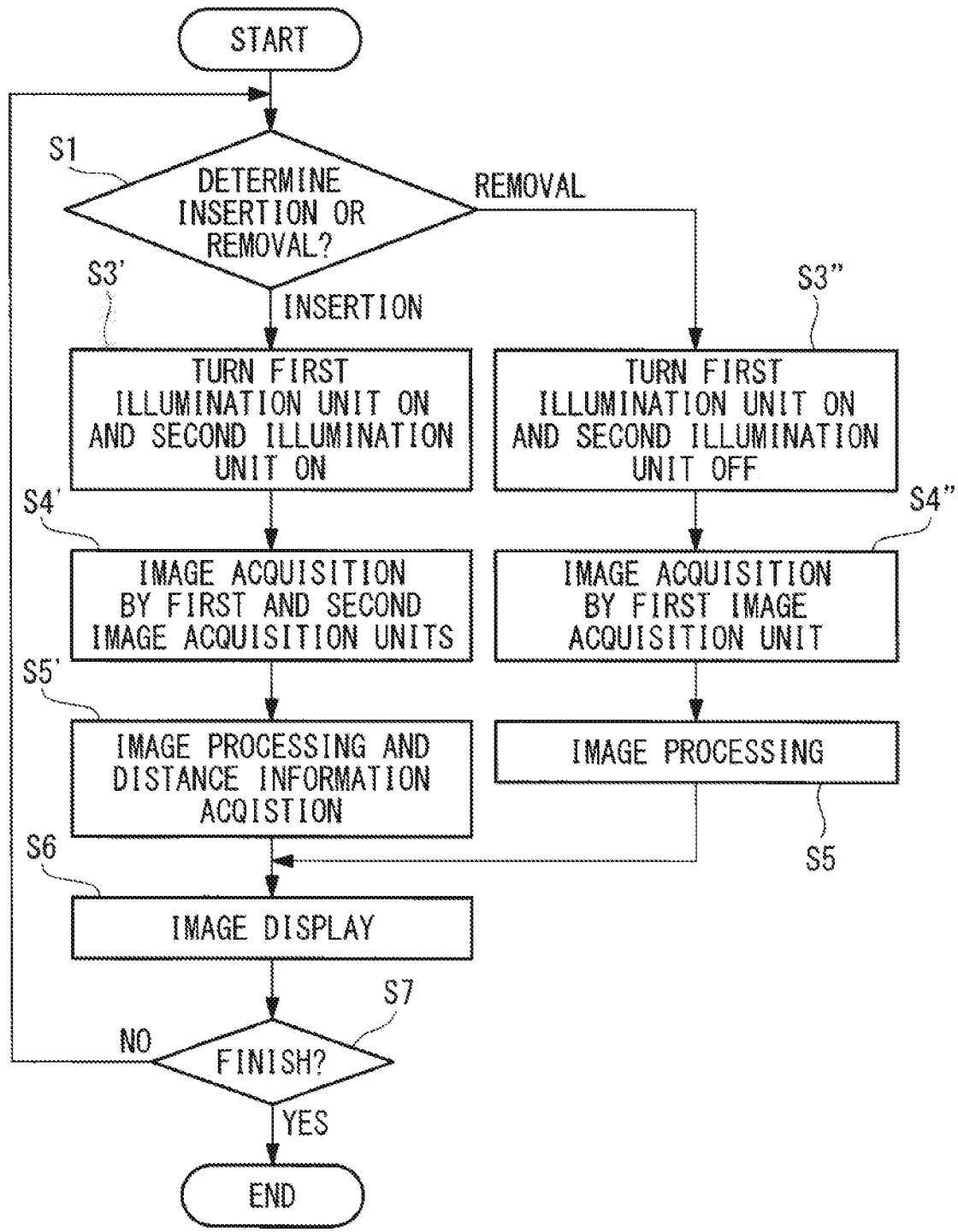
FIG. 14 is a flowchart for explaining the operation of the endoscope system shown in FIG. 9.

In order to realize this, as shown in FIGS. 13 and 14, the insertion portion 5 is provided with a visible-light-observation first illumination part 25, a distance-detection second illumination part 26, a visible-light-observation first image acquisition part 27, and a distance-detection second image acquisition part (range sensor) 28. If the insertion/removal determining part 17 determines that the insertion portion 5 is in the inserting state, the illumination controller 15 actuates both the first illumination part 25 and the second illumination part 26 (Step S3'). Then, both the first image acquisition part 27 and the second image acquisition part 28 are made to acquire images (Step S4'). The image processor 18 obtains distance information from image signals obtained in the second image acquisition part 28 (Step S5'). The distance information is displayed on the image display part 4 together with an image acquired, by the first image acquisition part 27.

Distance measurement is performed at the time of insertion of the insertion portion 5 into the body cavity, thereby making it possible to obtain information on the distances between the distal end of the insertion portion 5 and respective sections in the body cavity and to more accurately confirm, in particular, the direction in which the body cavity extends.

On the other hand, if the insertion/removal determining part 17 determines that the insertion portion 5 is in the removing state, the illumination controller 15 actuates only the first illumination part 25 (Step S3"). The first image acquisition part 27 is made to acquire an image (Step S4").

The image acquired by the first image acquisition part 27 is displayed on the image display part 4.

As a method for obtaining distance information, it is also possible to adopt a method for performing stereo measurement at respective positions on the inner wall of the body cavity.

Figure 15:
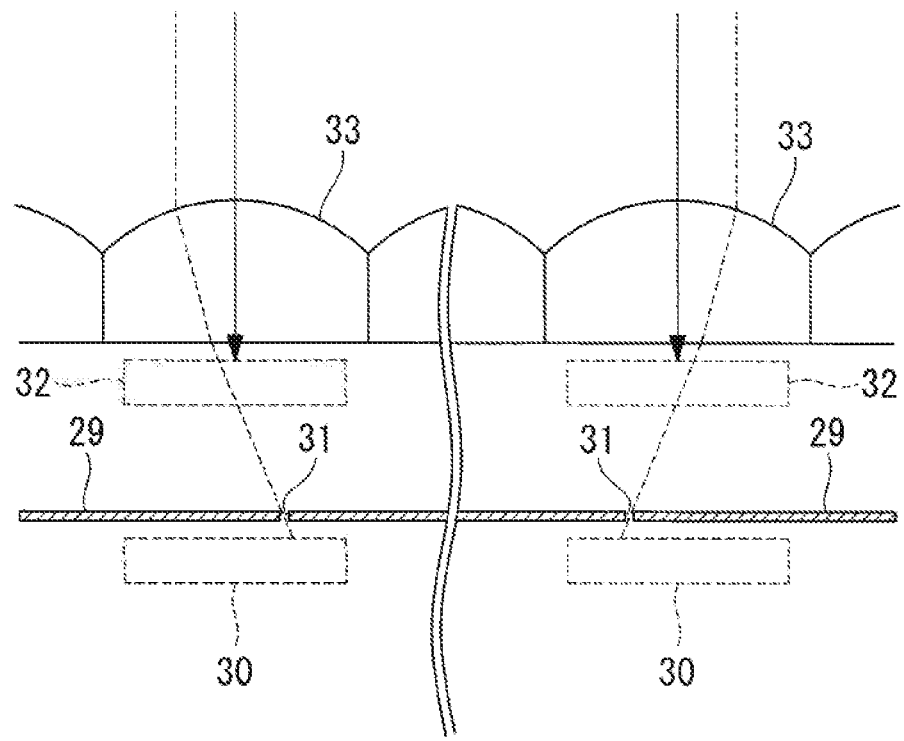
FIG. 15 is a longitudinal sectional view showing an example image acquisition element used in another example of the endoscope system shown in FIG. 9.

For example, as shown in FIG. 15, as an image acquisition element, it is possible to adopt an image acquisition element in which masks 29 are disposed on the layer under visible-light-observation photodiodes 32, and stereo-measurement photodiodes (range sensors) 30 are disposed on the layer under the masks 29. In the figure, reference sign 33 denotes microlenses.

Figure 16:
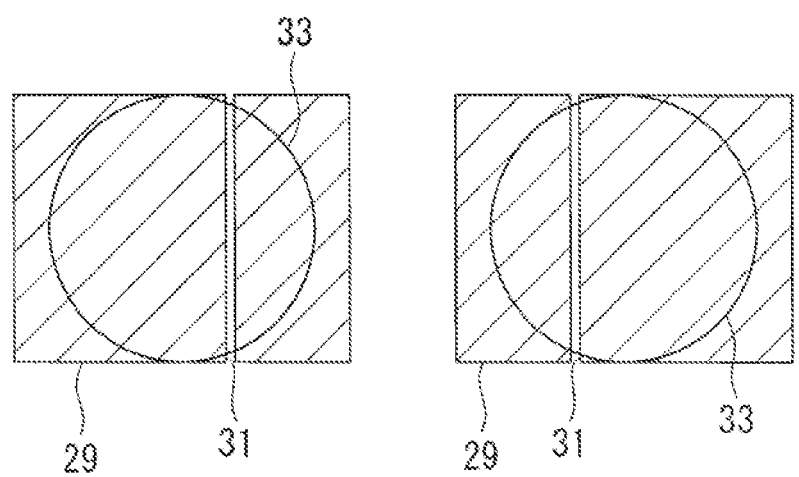
FIG. 16 is a plan view showing example masks provided in the image acquisition element, shown in FIG. 15.

As the masks 29, as shown in FIG. 16, it is possible to use masks that have slits 31 disposed at positions biased in a right or left direction from the center and that are alternately disposed. Then, a white-light source for visible-light observation and an infrared-light source for emitting near-infrared or infrared light are disposed at the distal end of the insertion portion 5 and are actuated at the same time.

Accordingly, whereas white light reflected at the inner-wall of the body cavity is detected by the visible-light-observation photodiodes 32 of the image acquisition element, near-infrared light or infrared light is transmitted through the visible-light-observation photodiodes 32, and only light passing through the slits 31 in the masks 29 is detected by the stereo-measurement photodiodes 30 on the lowermost layer. Because the light detected by the photodiodes 30 corresponding to the masks 29 having the slits 31 biased in different directions has a parallax, the image is viewed separately by both right and left eyes, thereby making it possible to three-dimensionally observe the inner wall of the body cavity.

Therefore, when it is detected that the insertion portion 5 is in the inserting state, the infrared-light source is actuated, and an image having parallax, acquired by the stereo-measurement photodiodes 30, is displayed, thereby making it possible for the operator to accurately recognize the depth of (distance to) the body cavity and to make the insertion portion 5 more accurately advance toward the end of the body cavity.

As a result, the following aspect is read from the above described embodiment of the present invention.

According to one aspect, the present invention provides an endoscope system including: an endoscope that is provided with an insertion portion that is configured to be inserted into a body cavity and an image acquisition part that is configured to acquire, at a distal end of the insertion portion, an image of the inside of the body cavity; an insertion/removal detector that is configured to detect a relative movement direction of the insertion portion with respect to the body cavity; an image generator that is configured to generate image information suitable for a movement mode of the insertion portion based on the relative movement direction detected by the insertion/removal detector; and an image display part that is configured to display the image information generated by the image generator.

According to this aspect, when, the insertion portion of the endoscope is inserted into the body cavity, the insertion/removal detector detects that the relative movement direction of the insertion portion with respect to the body cavity is the direction in which the insertion portion is being inserted into the body cavity, and the image generator generates image information suitable for the movement, mode of the insertion portion when the insertion portion is being inserted into the body cavity. Furthermore, when the insertion portion is in removing from the body cavity, after the insertion portion is inserted into the body cavity up to the end thereof, the insertion/removal detector detects that the relative movement direction of the insertion portion with respect to the body cavity is the direction in which the insertion portion is being removed from the body cavity, and the image generator generates image information suitable for the movement mode of the insertion portion when the insertion portion is being removed from the body cavity.

Then, the image information suitable for the movement mode according to each of the relative movement directions is displayed on the image display part, thereby allowing an operator to obtain a lot of information from the images and making it possible to improve the manipulability at the time of insertion and to improve the ease of observation at the time of removal.

In the above-described aspect may further include an image-acquisition controller that is configured to control the image-acquisition part, wherein based on the relative movement direction, the image-acquisition controller may control a frame rate of the image acquisition part or the image generator may process a tone of the image acquired by the image acquisition part.

In the above-described aspect may further include an image-acquisition controller that is configured to control the image-acquisition part, wherein based on the relative movement direction, the image-acquisition controller may control a frame rate of the image acquisition part.

In the above-described aspect, based on the relative movement direction, the image generator may process a tone of the image acquired by the image acquisition part.

In the above-described aspect, the image-acquisition controller may control the image acquisition part such that the frame rate is increased when the relative movement-direction detected by the insertion/removal detector is a direction of the insertion portion being inserted into the body cavity, compared with when the relative movement direction detected by the insertion/removal detector is a direction of the insertion portion being removed from the body cavity.

In the movement mode when the insertion portion is inserted into the body cavity, the distal end of the insertion portion is generally made to quickly advance while searching for an insertion direction; thus, images acquired by the image acquisition part significantly change. According to this aspect, when the insertion portion is inserted into the body cavity, because the image acquisition part is made to acquire images at a higher frame rate than when the insertion portion is in removing from the body cavity, it is possible to display, on the image display part, a moving image that smoothly changes even if the insertion portion is frequently moved.

Accordingly, the operator, who performs an insertion operation while viewing the image display part, can perform swift insertion work by searching for an insertion direction of the insertion portion with no stress due to the smoothly-changing moving image.

On the other hand, when the insertion portion is in removing from the body cavity, because the image acquisition part is made to acquire images at a lower frame rate than when the insertion portion is inserted into the body cavity, high-resolution images can be acquired. Accordingly, the operator can observe, in detail with the high-resolution images displayed on the image display part, the presence or absence of a lesion and the state of the lesion in the body cavity.

Furthermore, in the above-described aspect, the image-acquisition controller may control the image acquisition part such that signals of a plurality of pixels are added and then output when the relative movement direction detected by the insertion/removal detector is the direction of the insertion portion being inserted into the body cavity.

By doing so, even when the frame rate is increased, thus reducing the exposure time, the sensitivity can be improved and compensated for through pixel addition. Furthermore, the number of image signals to be output, from the image acquisition part is reduced to reduce the time required for image processing, thereby making it possible to rapidly perform processing with no delay even when the frame rate is increased. Accordingly, a smoothly-changing moving image can be presented in response to a quick movement of the insertion portion.

Furthermore, in the above-described aspect, the image generator may process an image acquired by the image acquisition part such that the image has a low-brightness-visibility emphasizing tone when the relative movement direction detected by the insertion/removal detector is the direction of the insertion portion being inserted into the body cavity, compared with when the relative movement direction is the direction of the insertion portion being removed from the body cavity.

When the insertion portion is relatively moved in the direction in which it is inserted into the body cavity, a field of view of the image acquisition part, which is provided at the distal end of the insertion portion, is directed forward in the longitudinal direction of the body cavity, and a low-brightness region in the vicinity of a center far from the distal end of the insertion portion is a region that is located in the direction in which the distal end of the insertion portion is to be inserted and that is most focused on by the operator.

According to this aspect, because image processing is performed so as to have a low-brightness-visibility emphasizing tone, thus increasing the number of the gradation values in a low-brightness region and making it possible to accurately determine the traveling direction of the insertion portion on the basis of a high-definition image in which the contrast is increased toy assigning many gradation values to the low-brightness region.

Furthermore, in the above-described aspect, the image generator may process an image acquired by the image acquisition part such that the image has a medium-brightness-visibility emphasizing tone when the relative movement-direction detected by the insertion/removal detector is the direction of the insertion portion being removed from the body cavity, compared with when the relative movement direction is the direction in which the insertion portion being inserted into the body cavity.

When the insertion portion is relatively moved in the direction in which it is in removing from the body cavity, a field of view of the image acquisition part, which is provided at the distal end of the insertion portion, is directed forward in the longitudinal direction of the body cavity, thus acquiring an image having low brightness in the vicinity of a center far from the distal end of the insertion portion and medium or higher brightness at the surrounding. Then, the inner wall of the body cavity located at the surrounding region having the medium or higher brightness is a region most focused on by the operator in order to observe the presence or absence of a lesion or the state thereof.

According to this aspect, because image processing is performed, so as to haw a medium-brightness-visibility emphasizing tone, thus assigning many gradation values to the medium-brightness region and making it possible to perform high-definition observation of the lesion portion.

Furthermore, the above-described aspect may further include a range sensor that is configured to obtain distance information from the distal end of the insertion portion to the body cavity, wherein, only when the relative movement direction detected by the insertion/removal detector is the direction of the insertion portion being inserted into the body cavity, the image generator may generate image information that includes the distance information obtained by the range sensor.

By doing so, image information that includes distance information is presented on the image display part, thereby making it possible for the operator to accurately recognize the depth of (distance to) the body cavity and to make the insertion portion more accurately advance toward the end of the body cavity.

REFERENCE SIGNS LIST 1 endoscope system
2 endoscope
4 image display part
5 insertion portion
8 image acquisition part
9 insertion/removal detector
18 image processor (image generator)
23 distance-detection image acquisition element (range sensor)
28 second image acquisition part (range sensor)
30 stereo-measurement photodiode (range sensor)

The invention claimed is:

1. An endoscope system comprising:
    an endoscope that is provided with an insertion portion that is configured to be inserted into a body cavity and an image acquisition part that is configured to acquire, at a distal end of the insertion portion, an image of the inside of the body cavity;
    an insertion/removal detector that is configured to detect a relative movement direction of the insertion portion with respect to the body cavity;
    an image generator that is configured to generate image information by processing a gradation correction process that assigns more gradation values to a first region rather than to a second region to an image acquired by the image acquisition part when the relative movement direction detected by the insertion/removal detecting unit is the direction of the insertion portion being inserted into the body cavity, compared with when the relative movement direction is the direction of the insertion portion being removed from the body cavity; and
    an image display part that is configured to display the image information generated by the image generator.

2. The endoscope system according to claim 1, wherein the gradation correction process by using a tone curve that reduces gradation value assigned as the brightness increases from zero.

3. An endoscope system comprising:
    an endoscope that is provided with an insertion portion that is configured to be inserted into a body cavity and an image acquisition part that is configured to acquire, at a distal end of the insertion portion, an image of the inside of the body cavity;
    an insertion/removal detector that is configured to detect a relative movement direction of the insertion portion with respect to the body cavity;
    an image generator that is configured to generate image information by processing a gradation correction process that assigns more gradation values to a second region rather than to a first region to an image acquired by the image acquisition part when the relative movement direction detected by the insertion/removal detector is the direction of the insertion portion being removed from the body cavity, compared with when the relative movement direction is the direction of the insertion portion being inserted into the body cavity; and an image display part that is configured to display the image information generated by the image generator.

4. The endoscope system according to claim 3, wherein the gradation correction process by using an S-shaped tone curve.

5. An image processing method comprising:
image acquisition step for acquiring an image of inside of a body cavity at a distal end of an insertion portion of an endoscope that is inserted into the body cavity;
an insertion/removal detection step for detecting a relative movement direction of the insertion portion with respect to the body cavity;
an image generation step for generating image information for a movement mode of the insertion portion based on the relative movement direction; and
an image display step for displaying the image information,
wherein in the image generating step,
generating the image information by processing a gradation correction process that assigns more gradation values to a first region rather than to a second region to the acquired image when the relative movement direction detected by the insertion/removal detection step is the direction of the insertion portion being inserted into the body cavity, compared with when the relative movement direction is the direction of the insertion portion being removed from the body cavity; and
generating the image information by processing a gradation correction process that assigns more gradation values to the second region rather than to the first region to the acquired image when the relative movement direction detected by the insertion/removal detection step is the direction of the insertion portion being removed from the body cavity, compared with when the relative movement direction is the direction of the insertion portion being inserted into the body cavity.

* * * * *